United States Patent [19]

Bradshaw et al.

[11] Patent Number: 5,039,419

[45] Date of Patent: Aug. 13, 1991

[54] SULFUR-CONTAINING HYDROCARBON COMPOUNDS AND PROCESS OF USING SAME IN RECOVERING AND CONCENTRATING DESIRED IONS FROM SOLUTIONS THEREOF

[75] Inventors: Jerald S. Bradshaw; Reed M. Izatt; Bryon J. Tarbet; Krzysztof Krakowiak; Jan F. Biernat; Ronald L. Bruening, all of Provo, Utah

[73] Assignee: Brigham Young University, Provo, Utah

[21] Appl. No.: 587,254

[22] Filed: Sep. 24, 1990

Related U.S. Application Data

[63] Continuation-in-part of Ser. No. 218,156, Jul. 13, 1988, Pat. No. 4,959,153.

[51] Int. Cl.$^5$ .................... B01D 39/00; B01D 15/08
[52] U.S. Cl. .................... 210/502.1; 55/386; 210/198.2; 210/670; 210/679; 210/681; 210/688; 502/401; 556/427
[58] Field of Search ............... 210/670, 679, 681, 688, 210/502.1, 198.2; 556/427; 502/401, 402; 55/386

[56] References Cited

U.S. PATENT DOCUMENTS

| | | | |
|---|---|---|---|
| 3,186,965 | 6/1965 | Plueddemann | 556/427 |
| 4,005,024 | 1/1977 | Rodriguez et al. | 556/427 |
| 4,650,784 | 3/1987 | Ramsden et al. | 210/502.1 |
| 4,959,153 | 9/1990 | Bradshaw et al. | 210/670 |

Primary Examiner—Robert A. Dawson
Assistant Examiner—Sun Uk Kim
Attorney, Agent, or Firm—Terry M. Crellin

[57] ABSTRACT

The invention has compositions of matter and process aspects.

The compositions of matter aspect relate to two classes of new organic compounds, viz., A. intermediates which are sulfur-containing hydrocarbons covalently bonded to trialkoxysilane and B. that class of intermediates covalently bonded to an inorganic matrix, e.g., silica, silica gel, glass, glass fibers, alumina, nickel oxide, zirconia, and titania. The process aspect comprises two processes, viz., (1) a process for making the two new classes of compounds A and B, and (2) the process of removing and concentrating certain ions, such as noble metal ions and other transition metal ions, from solution thereof admixed with other ions which may be present in much higher concentrations by forming a complex of the desired ion(s) with a compound of class B, e.g., by flowing the solution through a chromatography column packed with the compound, breaking the complex, e.g., by flowing a receiving liquid through the column in much smaller amount than the amount of solution passed through it to remove and concentrate the desired ion(s) in solution in the receiving liquid and recovering the desired ion(s) from the receiving liquid.

10 Claims, 1 Drawing Sheet

Glass wool

Silica-O-Si(Y)(Z)-(CH$_2$)$_a$(ACH$_2$CHR$^1$CH$_2$)$_b$(BCHR$^2$CH$_2$)$_c$(DCHR$^2$CH$_2$)$_d$E Glass wool

SULFUR-CONTAINING HYDROCARBON COMPOUNDS AND PROCESS OF USING SAME IN RECOVERING AND CONCENTRATING DESIRED IONS FROM SOLUTIONS THEREOF

This application is a continuation-in-part of the previously filed application; Ser. No. 218,156, filed July 13, 1988, now U.S. Pat. No. 4,959,153.

The present invention has composition and process aspects.

The composition aspect relates to two classes of new organic compounds:

A. an intermediate sulfur-containing hydrocarbon covalently bonded to a trialkoxysilane, and B. that class of intermediates covalently bonded to an inorganic matrix such as silica or silica gel among others.

The process aspect comprises two processes, viz., (1) a process for making the two new organic compounds and (2) the process of removing and concentrating certain ions, such as noble metal ions and other transition metal ions, from solutions thereof admixed with other ions which may be present in much higher concentrations, by forming a complex of the desired ions with a compound of class B, e.g., by flowing such solutions through a chromatography column packed with a compound of class B, breaking the complex, e.g., by flowing a receiving liquid in much smaller volume than the volume of solution passed through the column to remove and concentrate the desired ions in solution in the receiving liquid, and recovering the desired ions from the receiving liquid.

BACKGROUND OF THE INVENTION

The fact is known that macrocyclic polythioethers and certain other sulfur-containing hydrocarbon ligands present as solutes in a solvent such as water are characterized by their ability to selectivity form strong bonds with the noble metal, platinum group metal, and mercury ions or groups of these ions present as solutes in the same solvent as described in articles by R. M. Izatt, R. E. Terry, L. D. Hansen, A. G. Avondet, J. S. Bradshaw, N. K. Dalley, T. E. Jensen and J. J. Christensen, *A CALORIMETRIC TITRATION STUDY OF UNI- AND BIVALENT METAL ION INTERACTION WITH SEVERAL THIA DERIVATIVES OF 9-CROWN-3, 12-CROWN-4, 15-CROWN-5, 18-CROWN-6, 24-CROWN-8, AND WITH SEVERAL OXATHIAPENTADECANES IN WATER OR WATER-METHANOL SOLVENTS AT 25° C.* Inorganica Chemica Acta, 1978, Vol. 30, 1–8 for the complexation of silver and mercury ions by open chain sulfur-containing hydrocarbons and by S. R. Cooper, *CROWN THIOETHER CHEMISTRY,* Accounts of Chemical Research, 1988, Vol. 21, 141–146 for the complexation of rhodium and silver ions by macrocyclic sulfur-containing ligands. However, researchers have not previously been able to incorporate sulfur-containing hydrocarbon ligands into separation systems where the behavior of the sulfur-containing ligands in the separation systems in comparison to that of the sulfur-containing ligand as a solute is unchanged and/or the sulfur-containing ligand will remain in the separation system. Articles such as those entitled *SILANE COMPOUNDS FOR SILYLATING SURFACES* by E. P. Plueddemann, in "Silanes, Surfaces and Interfaces Symposium, Snowmass, 1985," Ed. by D. E. Leyden, Gordon and Breach, Publishers, 1986, pp. 1–25 and *SILANE COUPLING AGENTS* by E. P. Plueddemann, Plenum Press, 1982, pp. 1–235 list many different types of organic materials which have been attached to silane compounds and discusses some of their properties. The preparation and uses of sulfur-containing hydrocarbons attached to silane or silica have not been disclosed in the above mentioned article or in any existing patents. Thus, the unique complexing properties of certain sulfur containing hydrocarbons and the ability to attach these sulfur-containing complexing agents to silica or silica gel without reducing their ability to complex certain metal ions is of utmost importance in the industrial use of the sulfur-containing hydrocarbon ligands. The process of the present invention accomplished this feat.

SUMMARY OF THE INVENTION

The two new organic compounds of the present invention comprise an intermediate ligand material and a final product comprising the ligand material covalently bonded to an inorganic support matrix. The intermediate ligand material comprises sulfur-containing hydrocarbons covalently bonded to a trialkoxysilane and are shown by the structural formula (1).

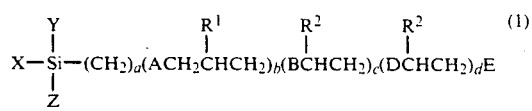

In formula (1), A is a member selected from the group consisting of O, OCH$_2$, S and SCH$_2$; B and D are members selected from the group consisting of O, OCH$_2$, S and SCH$_2$, with the proviso that if B is O or OCH$_2$, then D must be S or SCH$_2$ and if D is O or OCH$_2$, then B must be S or SCH$_2$; E is a member selected from the group consisting of H, SH, OH lower alkyl, and S[CH$_2$CH(R$^1$)CH$_2$A]$_b$(CH$_2$)$_a$SiXYZ; X is a member selected from the group consisting of Cl, OCH$_3$ or OC$_2$H$_5$; Y and Z are members selected from the group consisting of Cl, OCH$_3$, OC$_2$H$_5$, methyl, ethyl, and halogenated substituents thereof; R$^1$ is a member selected from the group consisting of H, SH, OH, lower alkyl, phenyl, naphthyl and pyridyl; R$^2$ is a member selected from the group consisting of H and lower alkyl; a is from 2 to about 10; b is 0 or 1; c is 1 to about 5; d is 0 to about 5.

The final product comprising the sulfur-containing, ligand intermediates covalently bonded to an inorganic matrix are show by the structural formula (2).

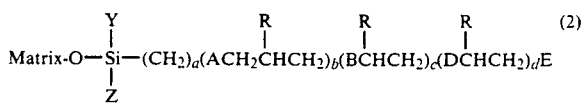

In formula (2), A is a member selected from the group consisting of O, OCH$_2$, S and SCH$_2$; B and D are members selected from the group consisting of O, OCH$_2$, S and SCH$_2$, with the proviso that if B is O or OCH$_2$, then D must be S or SCH$_2$ and if D is O or OCH$_2$, then B must be S or SCH$_2$; E is a member selected from the group consisting of H, SH, OH, lower alkyl, and S[CH$_2$CH(R$^1$)CH$_2$A]$_b$(CH$_2$)$_a$SiYZ(O-matrix); Y and Z are members selected from the group consisting of Cl, OCH$_3$, OC$_2$H$_5$, O-matrix methyl, ethyl and halogenated substituents thereof; R$^1$ is a member selected from the group consisting of H, SH, OH, lower alkyl, phenyl, naphthyl and pyridyl; $R^2$ is a member selected from the group consisting of H and lower alkyl; a is from 2 to about 10; b is 0 or 1; c is 1 to about 5; d is 0 to about 5; and matrix is selected from the group consisting of silica, silica gel, glass, glass fibers, alumina, nickel oxide, zirconia, and titania.

In particularly preferred embodiments of both the intermediate ligand material and the final product comprising the ligand material as given by formulas (1) and (2) above, the constituent identified by the letter "A" in the formulas is oxygen.

The process of producing the new compounds of formula (1) and formula (2) are described fully hereafter.

The process of selectively and quantitatively removing and concentrating a selected ion or group of ions of the noble metal type, e.g., gold, silver; the platinum metals, e.g., platinum, palladium, rhodium and iridium; and, when noble and platinum metals are not present, ions of mercury, lead, zinc, and other transition metals, present at low concentrations from a plurality of other ions in a multiple ion solution in which the other ions may be present at much higher concentrations comprises bringing the multiple ion solution into contact with a compound of formula (2) of the invention which causes the desired ion(s) to complex with said compound, breaking the complex with a receiving liquid which takes the ion(s) into solution, and recovering the ion(s) therefrom.

The compounds of formula (2) are characterized by high selectivity for and removal of desired metal ions or groups of metal ions such as the noble metal ions present at low concentrations from the source phase containing a mixture of these metal ions with the ions one does not desire to remove present in much greater concentrations in the solution, in a separation device such as a column through which the solution is flowed. The process of selectively removing and concentrating the desired ion(s) is characterized by the ability to quantitatively complex from a large volume of solution the desired ion(s) when they are present at low concentrations. The ions are recovered from the separation column by flowing through it a small volume of a receiving phase which contains a solubilized reagent which need not be selective, but which will strip the ions from the ligand quantitatively. The recovery or the desired metal ions from the receiving phase is easily accomplished by well known procedures.

The preferred embodiment disclosed herein involves carrying out the process by bringing a large volume of the multiple ion solution into contact with a compound of formula (2) in a separation column. The multiple ion solution passes through the column and desired ions form a complex with the compound. Thereafter, a smaller volume of a receiving liquid is flowed through the column to break the complex by chemical or thermal means. The receiving liquid dissolves the desired ions and carries them out of the column. Other equivalent apparatus may be used instead of a column, e.g., a slurry which is filtered, washed with a receiving liquid to break the complex and recover the desired ion. The desired metal ions are then recovered from the receiving phase by well known procedures.

More particularly, the process comprises forming a covalent chemical bond between an inorganic matrix such as silica or silica gel, and at least one of the compounds of formula (1), placing the resulting bonded compound of formula (2) in a contacting device such as a tall column, causing a large volume of the mixture of ions to flow through the column where the desired metal ions complex with the bonded silica which separates them from the rest of the mixture which flows out of the column, then flowing a small volume of the receiving liquid through the column to break the complex and dissolve and carry out of the column the desired metal ion(s). The desired metal ions are then recovered from the receiving liquid by well known procedures.

The process of making the compounds represented by formula (1) and formula (2) is also part of the invention.

BRIEF DESCRIPTION OF THE FIGURE

The invention will be described and illustrated by reference to a drawing in which.

DESCRIPTION OF PREFERRED EMBODIMENTS OF THE INVENTION

Figure 1:
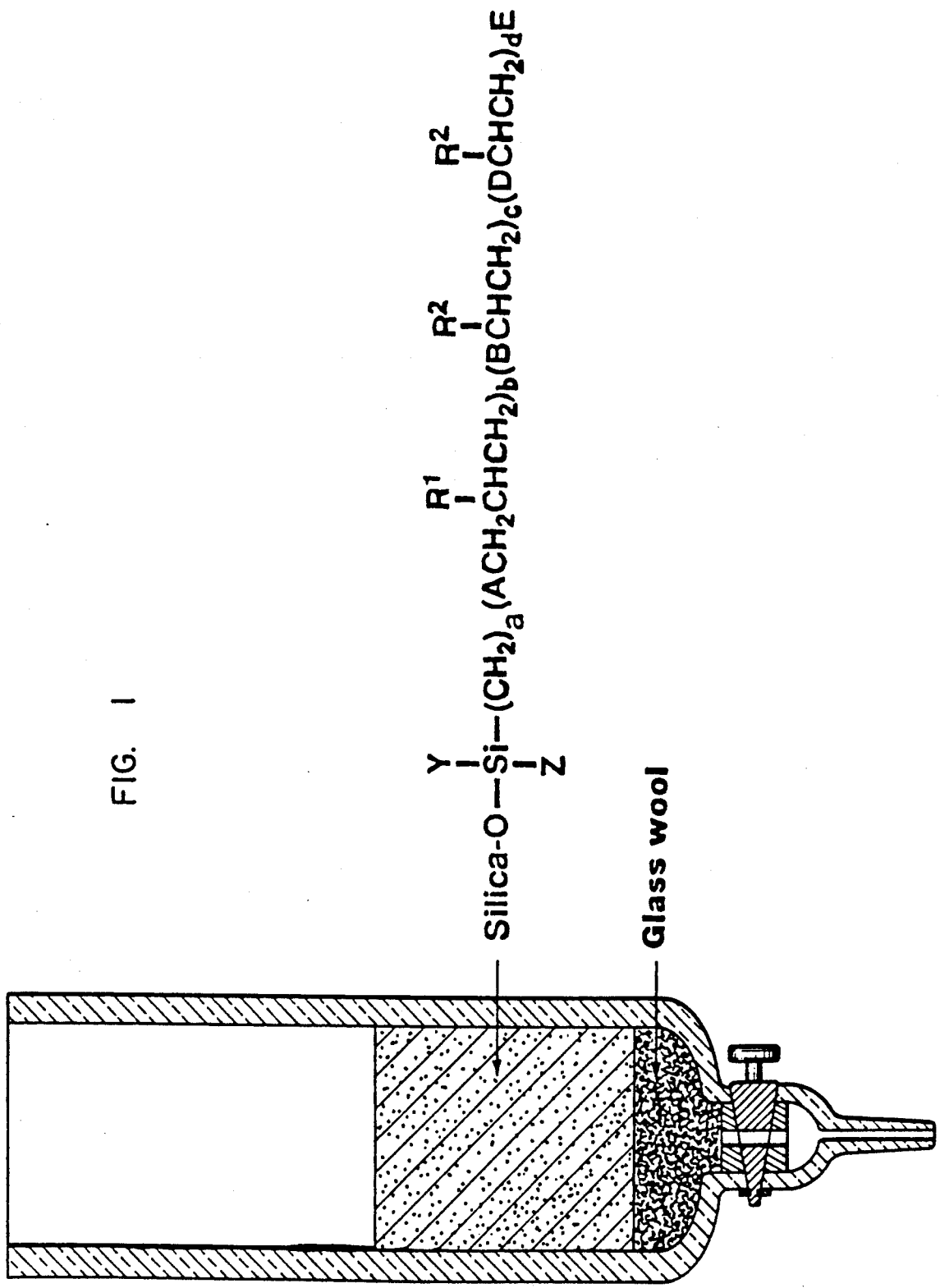
FIG. 1 represents schematically a suitable column for holding the silica bonded sulfur-containing hydrocarbon ligand material through which a solution of metal ions can be flowed r complex selectively with a desired ion or group of ions in accordance with the invention.

The preferred embodiment of the ion-recovery process of the invention utilizes the new compounds represented by formula (2). The process of producing these new compounds and the intermediates represented by formula (1) are an important aspect of the present invention.

Sulfur-containing hydrocarbon ligands must be covalently bonded to the inorganic matrix in accordance with the invention. The compounds of formula (1) satisfy this requirement because they can be bonded to the matrix. One method of preparing the compounds of the class represented by formula (1), for example, is to react mercapto forms of the sulfur-containing hydrocarbon with a silane-containing epoxide such as glycidoxypropyl-trimethoxysilane shown in equation (3).

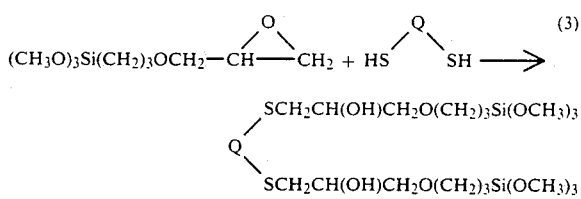

In equation (3) Q is a member selected from the group consisting of $(CH_2)_n$, $(CH_2)_m[S(CH_2)_m]_o$, $(CH_2)_m[O(CH_2)_m]_o$, n is from 2 to about 12, m is from 2 to about 5 and O is from 1 to about 4.

As a specific example, γ-glycidoxypropyl-trimethoxysilane and 1,2-ethanedithiol are used which are commercially available compounds. In the above reaction both mercaptan groups react with epoxides to form a compound containing two trimethoxysilane functions. The reaction can be carried out with a molar ratio of one mole of epoxide to one mole of mercaptan to give $(CH_3O)_3Si(CH_2)_3OCH_2CH(OH)CH_2SCH_2CH_2SH$ where the sulfur-containing hydrocarbon is 1,2-ethanedithiol.

The following two examples are given to illustrate compounds which have been made in accordance with formula (1) of the present invention. These examples are illustrative only, and are not comprehensive of the many different compounds which have been or can be made within the scope of the present invention.

EXAMPLE 1

In this example a sulfur-containing hydrocarbon bonded to a trialkoxysilane was made having the structure of formula (1) wherein a is 3, b is 1, c is 1, d is 0, $R^1$ is hydroxy, $R^2$ is hydrogen, A is oxygen, B is sulfur, D is not present since d is O, E is $SCH_2CH(OH)CH_2O(CH_2)_3Si(OCH_3)_3$, and X, Y and Z are methoxy groups.

1,2-Ethanedithiol (5.0 g, 0.05 mole) (Aldrich) was added to a stirred solution of 25.5 g (0.11 mole) of 3-glycidoxypropyltrimethoxysilane (Aldrich) in about 250 ml of toluene. A catalytic amount (1 ml) of freshly prepared 10% sodium methoxide in methanol was added to the solution and the solution was refluxed for 6 hours. The infrared spectrum of this mixture showed the absence of peaks at 2570 cm$^{-1}$ (SH) and greatly diminished peaks at 950 and 840 cm$^{-1}$ (epoxide) indicating that all the mercaptans had reacted with the slight excess of epoxide. This material was not further purified but was used in Example 3.

EXAMPLE 2

In this example, a sulfur-containing hydrocarbon bonded to a trialkoxysilane was made having the structure of formula (1) wherein a is 3, b is 1, c is 1, d is 1, $R^1$ is hydroxy, $R^2$ is hydrogen, A is oxygen, B is sulfur, D is sulfur, E is $SCH_2CH(OH)CH_2O(CH_2)_3Si(OCH_3)_3$, and X, Y and Z are methoxy groups.

2-Mercaptoethyl sulfide (0.71 g, 4.6 mmole) (Aldrich) was added to a stirred solution of 2.2 g (10 mmole) of 3-glycidoxypropyltrimethoxysilane in 250 ml of toluene. A catalytic amount (1 ml) of freshly prepared 10% sodium methoxide in methanol was added to the solution and the solution was refluxed for 6 hours. The infrared spectrum indicated that the reaction was completed as mentioned in Example 1. This material was used without purification in Example 4 below.

The compounds of formula (1) are covalently bonded to an inorganic matrix such as silica or silica gel by heating to effect a covalent bond as shown in equation 4.

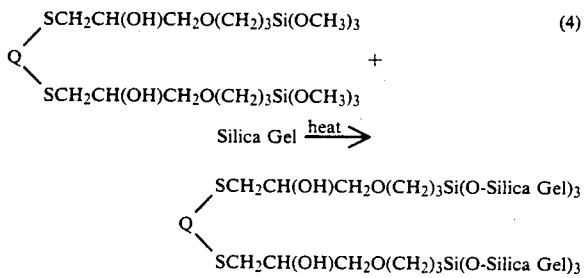

(4)

In equation (4), Q is a member selected from the group consisting of $(CH_2)_n$, $(CH_2)_m[S(CH_2)_m]_o$, $(CH_2)_m[O(CH_2)_m]_o$. n is from 2 to about 12, m is from 2 to about 5 and o is from 1 to about 4. The reaction can take place by first, dissolving the compound of formula (1) in a low boiling solvent such as methylene chloride, adding the silica or silica gel, removing the low boiling solvent then heating the coated silica or silica gel at about 120° C. for 3 to about 18 hours. A second procedure to cause the compounds of formula (1) to react with silica or silica gel is to heat the mixture of silica or silica gel and compound of formula (1) in a high boiling solvent such as toluene.

The following two examples are given to illustrate compounds which have been made in accordance with formula (2) of the present invention. These examples are illustrative only, and are not comprehensive of the many different compounds which have been or can be made within the scope of the present invention.

EXAMPLE 3

In this example a sulfur-containing hydrocarbon bonded to silica gel was made having the structure of formula (2) wherein a is 3, b is 1, c is 1, d is 0, $R^1$ is hydroxy, $R^2$ is hydrogen, A is oxygen, B is sulfur, D is not present since d is 0, E is $SCH_2CH(OH)CH_2O(CH_2)_3Si(O\text{-Silica Gel})_3$, and Y and Z are O-silica gel.

The toluene solution containing the compound of Example 1 was placed in a 1000 ml 3-necked sound bottom flask equipped with a mechanical stirrer and the solution was diluted to 400 m with additional toluene. Silica gel (132 g, 60–200 mesh) was added to the solution and the resulting mixture was slowly stirred and refluxed for 12 to about 24 hours. The sulfur-containing hydrocarbon bonded silica gel was filtered and air dried.

EXAMPLE 4

In this example, a sulfur containing hydrocarbon bonded to silica gel was made having the structure of formula (2) wherein a is 3, b is 1, c is 1, d is 1, $R^1$ is hydroxy, $R^2$ is hydrogen, A is oxygen, B is sulfur, D is sulfur, E is $SCH_2CH(OH)CH_2O(CH_2)_3Si(O\text{-Silica Gel})_3$, and Y and Z are O-silica gel.

The toluene solution containing the compound of Example 2 was treated as above in Example 3 to give 20 g of silica gel bound to the sulfur-containing material of Example 2.

The metal ion recovery and concentration process of the invention relates to the selective recovery of desired metal ions from mixtures thereof with other metal ions using the compounds of formula (2) of the invention as defined above. Effective methods of recovery and/or separation of metal ions, particularly the noble metal ions and platinum group metal ions, from other metal ions in water supplies, waste solutions, deposits and industrial solutions and silver recovery from waste solutions, e.g., from emulsions on photographic and X-ray film, represent a real need in modern technology. These ions are typically present at low concentrations in solutions containing other ions at much greater concentrations. Hence, there is a real need for a process to selectively recover and concentrate these metal ions. The present invention accomplishes this separation effectively and efficiently by the use of compounds selected from the families represented by formula (2).

The silica gel material of formula (2) is placed in a column as shown in FIG. 1. An aqueous solution containing the desired ion or ions, in a mixture of other ions which may be in a much greater concentration, is passed through the column. The flow rate for the solution may be increased by applying pressure (with a pump) on the top of the column or applying a vacuum in the receiving vessel. After the solution has passed through the column, a much smaller volume of a recovery solution, i.e. aqueous $Na_2S_2O_3$, aqueous $NH_3$, or aqueous NaI, which forms a stronger complex with the desired noble metal ions, is passed through the column.

This recovery solution contains only the desired metal ions in a concentrated form.

The following examples of separations of noble metal ions by the silica gel-bound sulfur-containing materials of Examples 3 and 4 are given as illustrations. These examples are illustrative only, and are not comprehensive of the many separations of noble metal, platinum group, and in some cases transition metal ions that are possible using the materials made within the scope of this invention.

EXAMPLE 5

In this example, 2 grams of the silica gel-bound sulfur-containing hydrocarbon of Example 3 was placed in a column as shown in FIG. 1. A 1000 ml solution of 3 ppm of Ag$^+$ in 1M aqueous M MgCl$_2$ was passed through the column using a vacuum pump to increase the flow rate. A 10 ml solution of 1 aqueous M Na$_2$S$_2$O$_3$ was passed through the column. An analysis of the recovery solution by atomic absorption spectroscopy (AA) showed that greater than 90% of the silver ions originally in the 1000 ml silver solution was in the 10 ml recovery solution.

EXAMPLE 6

A 1000 ml solution of 20 ppm Au(III) in saturated aqueous sodium chloride was passed through the column mentioned in Example 5. A 10 ml recovery solution of 5M aqueous NaI was passed through the column. An analysis of the recovery solution by AA spectroscopy showed that greater than 99% of the gold ion present in the original 1000 ml gold solution was in the recovery solution.

EXAMPLE 7

The experiment of Example 6 was repeated with 10 ppm Au(III) in an aqueous solution of 0.1M FeCl$_3$, saturated NaCl and 1M HCl. Again, greater than 99% of the gold ion in the original solution was found in the recovery solution.

EXAMPLE 8

The experiments of Examples 5, 6 and 7, using 2 grams of silica gel-bound sulfur-containing hydrocarbon of Example 4 rather than the sulfur material of Example 3, were repeated. In each case, greater than 99% of the silver or gold ions were found in the recovery solution.

EXAMPLE 9

The sulfur materials of Examples 3 and 4 have also been used to make separations among noble metal and platinum metal ions in solution. An example of this is the separation of Au(III) from Ag(I) in either 1M HNO$_3$, 1M HCl, or in saturated NaCl. By running the solution through the column until all of the ligand sites could potentially be filled with Au(III), a near quantitative separation was accomplished. No Ag(I) was detected in the regeneration solution of NaI. When a second column of Example 2 or 3 material was placed after the first column and where the ligand sites of the first column were filled with Au(III), Ag(I) ions can be isolated in the regeneration solution of the second column.

From the foregoing, it will be appreciated that the silica or silica gel-bound sulfur-containing hydrocarbon ligands of formula (2) of the present invention provide a material useful for the separation and concentration of the noble metal cations from mixtures of those cations with other metal cations. The noble metals can then be recovered from the concentrated recovery solution by standard techniques known in the science of these materials. Similar examples have also been successfully established for platinum group metal ions, and in the absence of noble and platinum metal ions for other transition metal ions.

Although the invention has been described and illustrated by reference to certain specific silica gel-bound sulfur-containing hydrocarbon ligands of formula (2) and processes of using them, analogs of these sulfur-containing hydrocarbon ligands are within the scope of the compounds and processes of the invention as defined in the following claims.

We claim:

1. A compound of formula

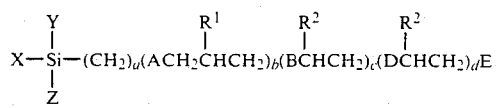

wherein
- R$^1$ is a member selected from the group consisting of hydrogen, hydroxy, thiohydroxy, lower alkyl, phenyl, naphthyl and pyridyl;
- R$^2$ is a member selected from the group consisting of hydrogen and lower alkyl;
- E is a member selected from the group consisting of hydrogen, hydroxy, thiohydroxy, lower alkyl and S[CH$_2$CH(R$^1$)CH$_2$A]$_b$(CH$_2$)$_a$SiXYZ;
- A is a member selected from the group consisting of O, OCH$_2$, S and SCH$_2$;
- B and D are members selected from the group consisting of O, OCH$_2$, S or SCH$_2$, with the proviso that if B is O or OCH$_2$ then D must be S or SCH$_2$ and if D is O or OCH$_2$ then B must be S or SCH$_2$;
- X is a member selected from the group consisting of chlorine, methoxy, ethoxy;
- Y and Z are members selected from the group consisting of chlorine, methoxy, ethoxy, methyl, ethyl and halogenated substituents thereof; and
- a is an integer from 2 to about 10; b is an integer of 0 or 1; c is an integer of 1 to about 5; d is an integer of 0 to about 5.

2. A compound as defined in claim 1 wherein a is 3, b is 1, c is 1, d is 0, R$^1$ is hydroxy, R$^2$ is hydrogen, A is oxygen, B is sulfur, E is SCH$_2$CH(OH)CH$_2$O(CH$_2$)$_3$SiXYZ, and X, Y and Z are methoxy.

3. A compound as defined in claim 1 wherein a is 3, b is 1, c is 1, d is 1, R$^1$ is hydroxy, R$^2$ is hydrogen, A is oxygen, B and D are sulfur, E is SCH$_2$CH(OH)CH$_2$O(CH$_2$)$_3$SiXYZ, and X, Y and Z are methoxy.

4. A compound as defined in claim 1 wherein E is

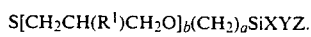

5. A compound of formula

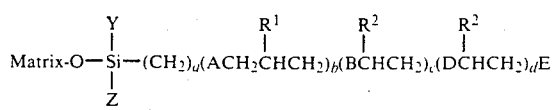

wherein

R¹ is a member selected from the group consisting of hydrogen, hydroxy, thiohydroxy, lower alkyl, phenyl, naphthyl and pyridyl;

R² is a member selected from the group consisting of hydrogen and lower alkyl;

E is a member selected from the group consisting of hydrogen, hydroxy, mercapto, lower alkyl and $S[CH_2CH(R^1)CH_2A]_b(CH_2)_aSiYZ$ (O-matrix);

A is a member selected from the group consisting of O, $OCH_2$, S and $SCH_2$

B and D are members selected from the group consisting of O, $OCH_2$, S and $SCH_2$, with the proviso that if B is O or $OCH_2$ then D must be S or $SCH_2$ and if D is O or $OCH_2$ then B must be S or $SCH_2$;

Y and Z are members selected from the group consisting of chlorine, O-matrix, methoxy, ethoxy, methyl, ethyl and halogenated substituents thereof;

matrix is selected from the group consisting of silica, silica gel, glass, glass fibers, alumina, nickel oxide, zirconia, and titania; and a is an integer from 2 to about 10; b is an integer of 0 or 1; c is an integer of 1 to about 5; d is an integer of 0 to about 5.

6. A compound as defined in claim 5 wherein a is 3, b is 1, c is 1, d is 0, R¹ is hydroxy, R² is hydrogen, A is oxygen, B is sulfur, matrix is silica; and E is $SCH_2CH(OH)CH_2O(CH_2)_3Si(O\text{-silica})_3$.

7. A compound as defined in claim 5 wherein a is 3, b is 1, c is 1, d is 0, R¹ is hydroxy, R² is hydrogen, A is oxygen, B is sulfur, matrix is silica gel; and E is $SCH_2CH(OH)CH_2O(CH_2)_3Si(O\text{-silica gel})_3$.

8. A compound as defined in claim 5 wherein a is 3, b is 1, c is 1, d is 1, R¹ is hydroxy, R² is hydrogen, A is oxygen, B and D are sulfur and E is $SCH_2CH(OH)CH_2O(CH_2)_3Si(O\text{-silica})_3$.

9. A compound as defined in claim 5 wherein a is 3, b is 1, c is 1, d is 1, R¹ is hydroxy, R² is hydrogen, A is oxygen, B and D are sulfur and E is $SCH_2CH(OH)CH_2O(CH_2)_3Si(O\text{-silica gel})_3$.

10. A compound as defined in claim 5 wherein E is $S[CH_2CH(R^1)CH_2O]_b(CH_2)_aSiYZ$(O-matrix).

* * * * *